United States Patent [19]

Richon et al.

[11] Patent Number: 4,688,436
[45] Date of Patent: Aug. 25, 1987

[54] AUTOMATIC PRESSURIZED FLUID MICRO-SAMPLING AND INJECTION DEVICE

[75] Inventors: Dominique Richon, Samoreau; Serge Laugier, Melun, both of France

[73] Assignee: Association pour la Recherche et le Developpement des Methodes et Processus Industrielles (A.R.M.I.N.E.S.), Paris, France

[21] Appl. No.: 852,547

[22] Filed: Apr. 16, 1986

[30] Foreign Application Priority Data

Apr. 19, 1985 [FR] France .................. 85 05999

[51] Int. Cl.⁴ .............................................. G01N 1/00
[52] U.S. Cl. ................................ 73/864.81; 73/863.71
[58] Field of Search ............ 73/864.81, 864.83, 864.84, 73/864.85, 864.86, 864.87, 23.1, 863.71, 863.72; 251/205

[56] References Cited

U.S. PATENT DOCUMENTS

| | | | |
|---|---|---|---|
| 2,014,642 | 9/1935 | Andrews | 251/205 |
| 3,118,300 | 1/1964 | Jenkins | 73/864.84 |
| 3,121,160 | 2/1964 | Burk | 73/23.1 |
| 3,166,939 | 1/1965 | Koeller et al. | 73/863.71 |
| 3,186,234 | 6/1965 | Solnick et al. | 73/863.71 |
| 3,213,669 | 10/1965 | Taft et al. | 73/23.1 |
| 3,327,520 | 6/1967 | Stapp, Jr. | 73/864.86 |
| 3,374,660 | 3/1968 | McKinney et al. | 73/864.86 |
| 3,401,564 | 9/1968 | Hrdina | 73/864.85 |
| 3,412,749 | 11/1968 | McAdams et al. | 137/240 |
| 3,438,243 | 4/1969 | Parks, Jr. et al. | 73/23.1 |
| 3,504,549 | 4/1970 | Davis et al. | 73/863.71 |
| 3,626,761 | 12/1971 | Haruki et al. | 73/864.81 |
| 3,889,538 | 6/1975 | Fingerle | 73/864.81 |
| 4,289,029 | 9/1981 | Sampson et al. | 73/863.11 |
| 4,362,046 | 12/1982 | Perrut et al. | 73/23.1 |

FOREIGN PATENT DOCUMENTS

| | | | |
|---|---|---|---|
| 477697 | 8/1915 | France | 251/205 |
| 2067722 | 8/1971 | France . | |
| 2476311 | 8/1981 | France . | |

*Primary Examiner*—Jerry W. Myracle
*Assistant Examiner*—Robert R. Raevis

[57] ABSTRACT

A device is provided for taking samples of a pressurized gas or liquid product, comprising a first through flow duct for the product to be sampled, a second through flow duct for a carrier gas or liquid, a communication conduit between said two ducts and a controllable means for normally closing and temporarily opening said communication passage. For injecting and vaporizing a liquid in analysis circuit, the device further comprises means for heating at least the downstream part of said communication conduit, i.e. that by which this latter is connected to said second duct through which said carrier gas or liquid flows.

15 Claims, 1 Drawing Figure

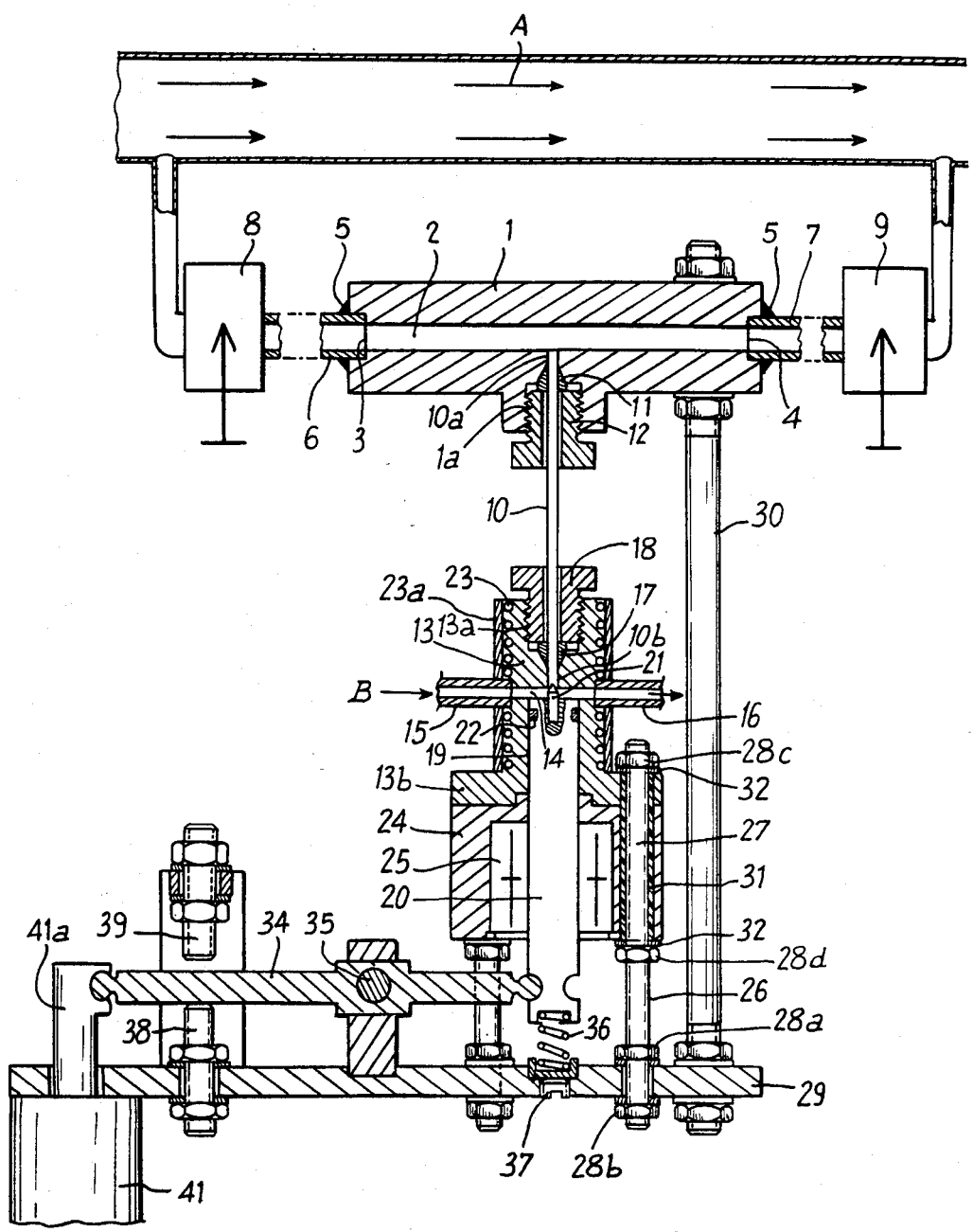
U.S. Patent   Aug. 25, 1987   4,688,436

AUTOMATIC PRESSURIZED FLUID MICRO-SAMPLING AND INJECTION DEVICE

BACKGROUND OF THE INVENTION

1. Field of the Invention

The invention relates to an automatic device for the micro-sampling and injection of a pressurized fluid with a view to an analysis, for example by chromotography, after transfer of the fluid sample into the flow of a carrier liquid or gas.

2. Description of the Prior Art

Taking samples of a fluid under high pressure is an extremely delicate procedure and the methods currently used for such sample taking have numerous drawbacks which have been indicated in the patent No. FR-A-2 476 311 of the applicant. This patent describes a device for taking samples of a pressurized gas or liquid product comprising a first duct through which the product to be sampled passes, a second duct through which the carrier gas or liquid passes, a conduit communicating between these two ducts and a member controllable for normally closing and temporarily opening the communication passage, such opening only taking place during the sample taking period. Such a device avoids the drawbacks associated with the prior known methods and it further provides a method for the automatic control of the manufacturing procedures in a loop. It provides for sampling at the output of a reactor analysis of the samples, and controlling the reactor operation to optimize results.

Such a known device has proved to be an extremely precious tool in so far as the sample taken alone is concerned. However, with such a device, the samples taken must be conveyed by a carrier, which is difficult or even impossible in gas chromotography if the sample taken is a liquid formed of compounds with high boiling points and if the carrier is a gas with a temperature substantially less than the boiling point of one or more of the compounds of the mixture,(slow or imperfect vaporization in the circuit of a gas chromatograph, used as apparatus for analyzing the sample, leads to inaccurate or false analysis).

An aim of the present invention is to provide a device of the above mentioned type for injecting and vaporizing a liquid in an analysis circuit.

SUMMARY OF THE INVENTION

This aim is obtained, in accordance with the invention, because means are provided for heating at least the downstream part of the communication conduit, that is to say that by which this latter is connected to the second duct through which the carrier flows.

The communication conduit is preferably formed by a capillary tube opening respectively, at its first and second ends, into the first and second ducts which are formed respectively in two separate parts, isolated thermally from each other, namely a sample taking head and a body, this body through which the second duct passes comprising the heating means. These heating means are advantageously formed by an electric resistance.

BRIEF DESCRIPTION OF THE DRAWING

One embodiment of the present invention will be described hereafter by way of nonlimiting example with reference to the accompanying drawing which is an axial sectional view of an automatic device for the microsampling and injection of a pressurized fluid in accordance with the invention.

DESCRIPTION OF THE PREFERRED EMBODIMENT

The device of the invention shown in the drawing is intended to be connected shuntwise to a duct through which a liquid or gas product A flows, which flow is shown by the arrows, or else directly to a container containing this product 1. The device comprises several separate parts assembled together. A first part, forming a sample taking head, is formed by a metal piece 1, of elongate shape, through which is formed axially a through bore 2 forming a duct through which the product A to be sampled flows. At both ends 3 and 4 of the through duct 2 are fixed, for example by welding 5, respective pipes 6 and 7 which are connected, through closure valves 8 and 9, to the main duct through which product A flows.

The sample taking head 1 is pierced transversely by a passage in which an end part 10a of a capillary tube 10 is engaged and fixed. This capillary tube 10 thus opens at its end into the through duct 2. It may be fixed in place by any appropriate means, for example by means of a cone-ring assembly 11 crushed by a screw 12 through which the capillary tube 10 passes and which is screwed into a tapped blind hole 1a formed in the lateral surface of the sample taking head 1.

The device of the invention further comprises a body 13, cylindrical in shape, in which the other end part 10b of the capillary tube 10 is engaged and fixed. Body 13 which is situated at a distance from the sample taking head 1 and is thus isolated thermally therefrom, has passing therethrough a pipe 14 forming a through duct for a carrier liquid or gas B. This duct 14 is connected, at both its ends, to two welded tubes 15 and 16 which allow the device to be connected to an analysis instrument, such as a chromatograph. Body 13 is pierced with a transverse hole which opens into the through duct 14 and in which the other end part 10b of the capillary tube 10 is engaged which thus emerges perpendicularly to the through duct 14. This end part is fixed in body 13, for example by means of conering assembly 17 and a screw 18 which is screwed into a tapped blind hole 13a formed in body 13. The tapped blind hole 13a of body 13 is situated opposite the blind hole 1a of the metal part 1, with which it is disposed coaxially. Where the tapped blind hole 13a of body 13 and the tapped blind hole 1a of the sample taking head 1 are coaxially disposed, as discussed above, the capillary tube is rectilinear. However, the arrangement of the two tapped holes 1a and 13a is presented only as a nonlimiting example of their relative disposition. They can occupy any other position relative to each other, with the capillary tube being appropriately curved, where necessary, to provide the required engagement with these two tapped holes.

Body 13 further has a bore 19 which is disposed coaxially with the capillary tube 10, on the other side of the through duct 14. In the bore 19 is mounted, for axial sliding, a metal rod 20 which has at its upper end a closure member formed, for example, by an axial tapered metal needle 21 whose pointed part is normally engaged in the orifice of the end part 10b of the capillary tube 10.

In a variant, this needle 21 could be replaced by any other closure member made from a relatively flexible and resilient material, such as a small cylinder made from a plastic material known under the name of "VITON", "KALREZ", etc.

Rod 20 slides sealingly in bore 19, the sealing being provided by an annular seal 22, made for example from polymer, which is housed in a transverse annular groove formed in the lateral surface of rod 20.

The metal body 13 in which the end portion 10b of the capillary tube 10 is engaged and fixed comprises heating means which may advantageously be formed by a helical electric resistance 23 which surrounds at least the portion of body 13 in which the end portion 10b of the capillary tube 10 is housed. This resistance may be housed in a helical groove formed in the external surface of the portion of body 13 surrounding the tapped hole 13a and the end portion 10b of tube 10. In the embodiment illustrated in the drawing, this heating resistance 23 also surrounds the portion of body 13 in which the end portion of the sliding rod 20 is engaged. This electric heating resistance 23 provides extra heating for the sample taken, when it is necessary. Preferably, the electric heating resistance 23 is enveloped in an external heat insulating sheath 23a.

Body 13 is extended, opposite the tapped blind hole 13a by a flange 13b on which is fixed a metal yoke 24 which serves as support for a tubular guide 25 which is preferably formed by a ball socket surrounding the sliding rod 20, for limiting the frictional forces opposing the translational movement of rod 20. The assembly comprising body 13 and yoke 24 is formed from several units 26, for example three in number, each comprising a threaded rod 27 passing through the flange 13b and yoke 24 and nuts 28a, 28b, 28c, 28d screwed onto this rod. Each threaded rod 27 is fixed, by means of the pair of nuts 28a, 28b, to a plate 29 itself assembled with part 1 by at least three assemblies 30 of the threaded rod and nut type. Moreover, it is firmly secured to the assembly formed by body 13 and yoke 24 by means of the other pair of nuts 28c, 28d.

Thermal insulation between the body 13, yoke 24 assembly and plate 29 is provided by using graphite guns 31, engaged on each threaded rod 27 in the zone where this latter passes through body 13 and yoke 24, and graphite washers 32 fitted on rod 27 and inserted between the nuts 28c, 28d and the opposite portions of body 13 and yoke 24.

The axial movement of the sliding rod 20 is controlled by an actuating device of any appropriate type carried by plate 29, this actuating device may more particularly comprise a lever 34 with two arms which is mounted on plate 29 for pivoting about an axis 35. One arm of lever 34 is coupled to rod 20, for example by means of a spherical end head engaging in a groove in rod 20. This rod 20 is pushed towards body 13, in the closure position, by a spring 36 inserted between its front face and plate 29. This spring 36 bears on a tension adjusting screw 37 which is screwed into plate 29.

The other arm of lever 34 extends between two adjustable stops 38, 39, carried by plate 29, for limiting the opening and closure travel of the closure needle 21 and the end of this arm is coupled to the rod 41a of an actuating cylinder 41 which may be controlled by a programmer (timer or microprocessor).

In the rest position, all the moving parts of the device occupy the position shown in the drawing. In this case, the sliding rod 20 is urged towards body 13 by spring 36 so that the closure needle 21 is engaged in the orifice facing the capillary tube 10, thus closing this latter. For this, the force exerted by spring 36 is adjusted so as to be higher than the antagonistic force which tends to move needle 21 away from capillary tube 10 and which is generated by the pressure of the fluid in this capillary tube. In the closed position, the pivoting lever 34 bears on the lower adjustable stop 38 which thus serves for adjusting the force exerted by needle 21 against the orifice of the capillary tube 10, which thus yields somewhat resiliently, while limiting the force exerted by spring 36.

When it is necessary to take a sample, the actuating cylinder 41 is actuated by the programmer, which causes rod 41a to extend. This causes lever 34 to pivot in a clockwise direction, about axis 35, and rod 20 and the closure needle 21 to slide downwardly. Because its lower end is then open, the capillary tube 10 becomes a communication passage between duct 2 through which product A passes and duct 14 through which carrier B passes. The result is that, during the whole time that the orifice of the capillary tube 10 is open, a certain amount of product A flows into the through flow duct 14 and is driven by carrier B towards an analysis instrument. The opening movement through axial sliding of rod 20 and needle 21 is limited by the abutment of the pivoting lever 34 against the upper adjustable stop 39. Adjustment of this stop consequently allows the size of the sample taken to be adjusted correspondingly.

It follows then from the foregoing description that during sampling the fluid which emerges at the end 10b of the capillary tube 10, for penetrating into duct 14 through which carrier B passes, may be heated by the resistance 23, if vaporization thereof is required, and it is immediately swept away by carrier B. The best result is obtained when the capillary tube 10 emerges perpendicularly into the duct 14 through which carrier B passes, substantially in the center of body 13.

What is claimed is:

1. A device for intoducing a sample of a pressurized fluid into a carrier liquid or gas for transferring said pressurized fluid to a means for analyzing the pressurized fluid, said device comprising:
    (a) a first duct for directing the pressurized fluid;
    (b) a second duct for directing the carrier liquid or gas;
    (c) a conduit having first and second openings, said conduit communicating with said first duct at said first opening, and communicating with said second duct at said second opening;
    (d) means for heating the portion of said conduit situated in the vicinity of said second opening; and
    (e) actuatable means for opening and closing said conduit, said means for opening and closing said conduit being associated with said conduit to close said conduit when not actuated, and to open said conduit when actuated, said means for opening and closing said conduit comprising:
        (i) a closure member associated with said conduit to close said conduit by blocking said second opening of said conduit, and to open said conduit by withdrawing from said second opening of said conduit; and
        (ii) a rod terminating in a first end and a second end, said closure member being mounted at said first end, and said rod being associated with said conduit for reciprocating motion, to retract from said second opening, thereby withdrawing said closure member from said second opening to open said conduit, and to advance toward said second opening, thereby pressing said closure member towards said second opening to block said conduit;

(f) a spring mounted at said second end of said rod to urge said rod toward said second opening to close said conduit when said opening and closing means is not actuated; and (g) means for actuating said opening and closing means.

2. The device as defined in claim 1 wherein said conduit is perpendicular to said second duct.

3. The device as defined in claim 1 wherein said heating means comprises a body in which said second duct is formed, said device further comprising:

(a) a sample taking head in which said first duct is formed, said sample taking head and said body being thermally isolated;

(b) a tubular guide surrounding said rod;

(c) a yoke surrounding said tubular guide, said body being mounted on said yoke;

(d) a plate;

(e) a plurality of support means affixed to said yoke, to said body, and to said plate for supporting said yoke and said body on said plate;

(f) a plurality of thermal insulating means interposed between said plurality of support means and said plate; and (g) connection means connecting said sample taking head to said plate, wherein said plate further supports said means for actuating said opening and closing means.

4. The device as defined in claim 3 wherein a portion of said conduit extends into said body, and wherein said heating means further comprises an electric resistance which surrounds at least a portion of said body into which said conduit portion extends.

5. The device as defined in claim 1 wherein said means for actuating said opening and closing means comprises a lever comprising two arms and an axis situated between said two arms, said lever being pivotable in a clockwise direction and in a counter-clockwise direction, and being actuatably associated with said rod so that rotation of said lever in one of said two directions actuates said rod to retract from said second opening, and rotation of said lever in the other of said two directions actuates said rod to advance toward said second opening.

6. The device as defined in claim 5, further comprising:

(a) a cylinder for actuating said lever; and (b) two opposed stops; one arm of said lever being situated between said two stops and actuated by said actuating cylinder, the other arm of said lever being mounted on said rod, wherein said two stops are adjustable to vary the distance between them and correspondingly vary the degree of rotation of said lever.

7. The device as defined in claim 6 further comprising a means for adjusting the force with which said spring urges said rod toward said second opening, said adjusting means comprising a screw mounted to rotate into and out of said plate.

8. The device as defined in claim 7 wherein said closure member comprises a tapered metal needle.

9. The device as defined in claim 1 wherein said conduit comprises a capillary tube.

10. The device as defined in claim 9 wherein said conduit is perpendicular to said duct.

11. The device as defined in claim 9 wherein said heating means comprises a body in which said second duct is formed, said device further comprising:

(a) a sample taking head in which said first duct is formed, said sample taking head and said body being thermally isolated;

(b) a tubular guide surrounding said rod;

(c) a yoke surrounding said tubular guide, said body being mounted on said yoke;

(d) a plate;

(e) a plurality of support means affixed to said yoke, to said body, and to said plate for supporting said yoke and said body on said plate;

(f) a plurality of thermal insulating means interposed between said plurality of support means and said plate; and (g) connection means connecting said sample taking head to said plate, wherein said plate further supports said means for actuating said opening and closing means.

12. The device as defined in claim 9 wherein said means for actuating said opening and closing means comprises a lever comprising two arms and an axis situated between said two arms, said lever being pivotable in a clockwise direction and in a counter-clockwise direction, and being actuatably associated with said rod so that rotation of said lever in one of said two directions actuates said rod to retract from said second opening, and rotation of said lever in the other of said two directions actuates said rod to advance toward said second opening.

13. The device as claimed in claim 12, further comprising:

(a) a cylinder for actuating said lever; and (b) two opposed stops; one arm of said lever being situated between said two stops and actuated by said actuating cylinder, the other arm of said lever being mounted on said rod, wherein said two stops are adjustable to vary the distance between them and correspondingly vary the degree of rotation of said lever.

14. The device as defined in claim 13 further comprising a means for adjusting the force with which said spring urges said rod toward said second opening, said adjusting means comprising a screw mounted to rotate into and out of said plate.

15. The device as defined in claim 14 wherein said closure member comprises a tapered metal needle.

* * * * *